United States Patent
Gu et al.

(10) Patent No.: US 11,999,769 B2
(45) Date of Patent: Jun. 4, 2024

(54) **METHOD FOR ISOLATING AND PURIFYING BACTERIOCIN AGAINST DRUG-RESISTANT *STAPHYLOCOCCUS AUREUS***

(71) Applicant: Zhejiang Gongshang University, Zhejiang (CN)

(72) Inventors: Qing Gu, Zhejiang (CN); Mengdi Dai, Zhejiang (CN); Qingqing Zhou, Zhejiang (CN); Ping Li, Zhejiang (CN); Danli Wu, Zhejiang (CN)

(73) Assignee: Zhejiang Gongshang University, Hangzhou (CN)

( * ) Notice: Subject to any disclaimer, the term of this patent is extended or adjusted under 35 U.S.C. 154(b) by 0 days.

(21) Appl. No.: 18/054,546

(22) Filed: Nov. 11, 2022

(65) Prior Publication Data
US 2023/0348544 A1  Nov. 2, 2023

(30) Foreign Application Priority Data

Apr. 30, 2022  (CN) ........................ 202210476584.4

(51) Int. Cl.
*C12P 21/02* (2006.01)
*C07K 14/335* (2006.01)

(52) U.S. Cl.
CPC ............ *C07K 14/335* (2013.01); *C12P 21/02* (2013.01)

(58) Field of Classification Search
CPC ........ C12P 21/00; C12P 21/02; C07K 14/195; C07K 14/335
See application file for complete search history.

(56) References Cited

FOREIGN PATENT DOCUMENTS

| | | | |
|---|---|---|---|
| CN | 108148789 A | | 6/2018 |
| CN | 111285925 A | | 6/2020 |
| CN | 112080445 A | | 12/2020 |
| KR | 20180041167 | * | 9/2020 ............ A23L 33/105 |

OTHER PUBLICATIONS

Zhao, Ruixiang, Yanqing Lu, Junjian Ran, Gang Li, Shuang Lei, Yang Zhu, Baocheng. Purification and characterization of bacteriocin produced by Lactobacillus rhamnosus zrx01. Food Bioscience, 38. (Year: 2020).*
Amberlite™ XAD™ 16N. Product Data Sheet. © 2008 Rohm and Haas Company. pp. 1-4 (Year: 2008).*
Wei, Y.; Wang, J.; Liu, Z.; Pei, J.; Brennan, C.; Abd El-Aty, A.M.Isolation and Characterization of Bacteriocin-Producing Lacticaseibacillus rhamnosus XN2 from Yak Yoghurt and Its Bacteriocin. Molecules 2022, 27, 2066. https://doi.org/10.3390/ (Year: 2022).*
Ramakrishnan Srinivasan & Dinesh K. Kumawat & Sunil Kumar & Anil Kumar Saxena. Purification and characterization of a bacteriocin from Lactobacillus rhamnosus L34. Ann Microbiol (2013) 63:387-392 DOI 10.1007/s13213-012-0486-8 (Year: 2013).*
Amersham Biosciences AB 2002. Gel Filtration. Principles and Methods. (Year: 2002).*
Yanqing, Lu, Ran Junjian, Zhao Ruixiang, Liang XinHong, et al. Optimal conditions and bacteriostatic activity of Lactobacillus rhamnosus. Journal of NW A&F Univ. Natural Science Edition, 2019. vol. 47, No. 4, pp. 119-128. (Year: 2019).*
Pengxin Ye, Jiawen Wang, Manman Liu, Ping Li **, Qing Gu * Purification and characterization of a novel bacteriocin from Lactobacillus paracasei ZFM54. LWT-Food Science and Technology. 2021. vol. 143, pp. 1-9 (Year: 2021).*
Jing-Zheng Songa, Chun-Feng Qiaoa, Song-Lin Li a, Yan Zhoua, Ming-Tsuen Hsiehb, Hong-Xi Xu. Rapid optimization of dual-mode gradient high performance liquid chromatographic separation of Radix et Rhizoma Salviae Miltiorrhizae by response surface methodology. Journal of Chromatography A. 1216 (2009) (Year: 2009).*
Dimitrijevic, R., M. Stojanovic, I. Zivkovic, A. Petersen, R.M. Jankov, L. Dimitrijevic, and M. Gavrovic-Jankulovic. The identification of a low molecular mass bacteriocin, rhamnosin A, produced by Lactobacillus rhamnosus strain 68. Journal of Applied Microbiology. 107 (2009) p. 2108-2115 (Year: 2009).*
Danli Wu, Mengdi Dai, Yongqing Shi, Qingqing Zhou, Ping Li*, and Qing Gu*. Purification and characterization of bacteriocin produced by a strain of Lacticaseibacillus rhamnosus ZFM216. Front. Microbiol. vol 13. p. 1-12. Nov. 10, 2022. (Year: 2022).*
Yizhen Zhao et al., Separation and Purification of a Bacteriocin Produced by Lactobacillus rhamnosus ZJ225 and Characteristic Study, Journal of Chinese Institute of Food Science and Technology, Jul. 2015, pp. 54-60, vol. 15, No. 7.
Ruixiang Zhao et al., Purification and characterization of bacteriocin produced by Lactobacillus rhamnosus zrx01, Food Bioscience, Sep. 2020, pp. 1-7.
Yanqing Lu et al., Optimal conditions and bacteriostatic activity of Lactobacillus rhamnosus, Journal of Northwest A&F University (Nat. Sci. Ed.), Sep. 2018, pp. 119-128, vol. 47, No. 4.
Wenxiong Zheng et al., Research progress on bacteriostatic effect and its application, China Food Additives, Jan. 2021, pp. 119-125.

* cited by examiner

*Primary Examiner* — Louise W Humphrey
*Assistant Examiner* — Jessica Faye Edwards (57) ABSTRACT

The present disclosure discloses a method for isolating and purifying *Lactobacillus rhamnosus* ZFM216 bacteriocin, the method including the following steps: preparing *L. rhamnosus* ZFM216 fermentation supernatant; treating the fermentation supernatant with macroporous adsorption resin method to obtain a crude protein extract; isolating the crude protein extract by gel chromatography to obtain a preliminary purified protein solution; and then performing purification by reversed-phase high performance liquid chromatography (HPLC) to obtain an *L. rhamnosus* ZFM216 bacteriocin solution. The present disclosure further provides use of the *L. rhamnosus* bacteriocin in anti-*Staphylococcus aureus*.

3 Claims, 8 Drawing Sheets

METHOD FOR ISOLATING AND PURIFYING BACTERIOCIN AGAINST DRUG-RESISTANT *STAPHYLOCOCCUS AUREUS*

CROSS-REFERENCE TO RELATED APPLICATIONS

The present application claims the benefit of Chinese Patent Application No. 202210476584.4 filed on Apr. 30, 2022, the contents of which are incorporated by reference herein in its entirety.

TECHNICAL FIELD

The present disclosure belongs to the field of food biotechnology, and in particular relates to *Lactobacillus rhamnosus* bacteriocin capable of effectively inhibiting drug-resistant *Staphylococcus aureus* D48 and a method for isolating and purifying the *L. rhamnosus* bacteriocin.

BACKGROUND

*S. aureus* is a susceptible pathogen that can cause body inflammation and even systemic infection. Spoilage of fruits and vegetables, dairy products, and meat are all potential sources of foodborne illness caused by *S. aureus*. *S. aureus* D48 is a methicillin-resistant *Staphylococcus*, is a foodborne pathogenic microorganism, and produces toxins that cause food poisoning. *S. aureus* survives a wide temperature range (7-48° C.) and pH (pH 4-10), and tolerates low water activity (aw 0.83-0.86) and very high salt concentration (15-20%). To prevent contamination and reproduction of *S. aureus* in food, food preservatives are commonly added, but excessive or long-term intake of chemical preservatives is prone to cause accumulation of toxicity and damage to the body. Hence, it is extremely urgent to develop new safe natural biological preservatives against resistant pathogenic microorganisms.

Lactic acid bacteria bacteriocin is a protein or polypeptide with a bacteriostatic effect produced by lactic acid bacteria, and can be used as a biological preservative for reducing pollution of foodborne pathogens, reducing economic loss caused by food spoilage, and improving the safety of food without changing the quality and flavor of the food. So far, lactic acid bacteria bacteriocin has been rarely developed in the food industry, and only nisin is widely used. Lactic acid bacteria bacteriocin products for inhibiting methicillin-resistant *S. aureus* have never been used commercially in the food industry. Therefore, it is of great significance to human health and socioeconomics to develop new lactic acid bacteria bacteriocin as a natural food bacteriostatic additive to control *S. aureus* contamination in food.

SUMMARY

To solve the above technical problems, the present disclosure provides a method for isolating and purifying *L. rhamnosus* ZFM216 bacteriocin, and discloses an anti-*S. aureus* D48 effect thereof.

To solve the above problems, the present disclosure provides a method for isolating and purifying *L. rhamnosus* ZFM216 bacteriocin, the method including the following steps:

1) Preparing *L. rhamnosus* ZFM216 fermentation supernatant:

inoculating MRS liquid medium with *L. rhamnosus* ZFM216 for fermentation, and centrifuging the fermentation broth to obtain the fermentation supernatant;

the preservation number of *L. rhamnosus* ZFM216 being CCTCC M 2020325;

2) treating the fermentation supernatant with macroporous adsorption resin method to obtain a crude protein extract; and 3) isolating the crude protein extract by gel chromatography to obtain a preliminary purified protein solution; and then performing purification by reversed-phase high performance liquid chromatography (HPLC) to obtain an *L. rhamnosus* ZFM216 bacteriocin solution.

As an improvement of the method for isolating and purifying the *L. rhamnosus* ZFM216 bacteriocin of the present disclosure, in step 1):

MRS liquid medium (pH 6.4) is inoculated with *L. rhamnosus* ZFM216 cultured to the logarithmic growth phase at an inoculum concentration of 2% (v/v) for performing stationary culture at 37° C. for 21 h; and the obtained fermentation broth is centrifuged at 8000 rpm, 4° C. for 30 min to obtain the fermentation supernatant.

As a further improvement of the method for isolating and purifying *L. rhamnosus* ZFM216 bacteriocin of the present disclosure, in step 2):

the fermentation supernatant is adsorbed with macroporous resin XAD-16 and eluted with 20% ethanol to obtain the eluate as the crude protein extract.

As a further improvement of the method for isolating and purifying *L. rhamnosus* ZFM216 bacteriocin of the present disclosure, in step 2):

1 L of *L. rhamnosus* ZFM216 fermentation supernatant is allowed to flow through XAD-16 macroporous resin at a flow rate of 2 mL/min, rinsed with 2 L of ultrapure water, and then eluted with 500 mL of 20% ethanol eluent at a flow rate of 2 mL/min, and the eluate corresponding to 20% ethanol is collected as the crude protein extract.

As a further improvement of the method for isolating and purifying *L. rhamnosus* ZFM216 bacteriocin of the present disclosure, during the isolation by gel chromatography in step 3):

the crude protein extract is subjected to gel chromatography with Sephadex LH-20 and eluted with ultrapure water as the eluent at a flow rate of 1 mL/min; and the eluate corresponding to the first absorption peak under the absorbance of 215 nm/280 nm is collected to obtain a preliminary purified protein solution.

As a further improvement of the method for isolating and purifying *L. rhamnosus* ZFM216 bacteriocin of the present disclosure, during purification by reversed-phase HPLC in step 3):

the preliminary purified protein solution is filtered through a 0.22 μm membrane, and precisely purified by preparative C18 reversed-phase HPLC (Waters 2998, USA) with a chromatographic column Sunfire™ Prep C18 (5 μm, 10×100 mm) at an injection volume of 5 mL;

0.05% TFA by volume of ultrapure water is added to the ultrapure water as mobile phase A, and 0.05% TFA by volume of acetonitrile is added to the acetonitrile as mobile phase B; the gradient elution procedure is as follows:

| Time (min) | Flow rate (mL/min) | Mobile phase A | Mobile phase B |
|---|---|---|---|
| 0 | 4 | 95 | 5 |
| 15 | 4 | 95 | 5 |
| 16 | 4 | 50 | 50 |
| 26 | 4 | 5 | 95 |
| 30 | 4 | 5 | 95 |
| 31 | 4 | 95 | 5 |
| 45 | 4 | 95 | 5 | the eluate corresponding to the 3rd absorption peak under the absorbance of 280 nm is collected, and named as peak 3 eluate, the peak 3 eluate contains L. rhamnosus ZFM216 bacteriocin.

TFA is trifluoroacetic acid.

As a further improvement of the method for isolating and purifying L. rhamnosus ZFM216 bacteriocin of the present disclosure, 5 mL of peak 3 eluate is freeze-dried (to a constant weight at −20° C.) to obtain L. rhamnosus ZFM216 bacteriocin, which is reconstituted with 1 mL of ultrapure water to obtain a peak 3 reconstituted solution, that is, the peak 3 reconstituted solution is an L. rhamnosus ZFM216 bacteriocin solution.

The present disclosure further provides use of the L. rhamnosus bacteriocin prepared by any of the above methods in anti-S. aureus.

Note: "methicillin resistance" in the present disclosure means resistance to methicillin.

The L. rhamnosus ZFM216 bacteriocin of the present disclosure can effectively inhibit S. aureus D48 with a minimum inhibitory concentration of 0.50 mg/mL, and a bacteriostatic action mode of destroying the cell membrane. The ATP level in S. aureus D48 cells treated with the bacteriocin decreases rapidly within 5 min. The conductivity of an S. aureus D48 suspension treated with the bacteriocin increases to the highest value within 5 min. The fluorescence intensity of an S. aureus D48 suspension treated with the bacteriocin increases rapidly. When the S. aureus D48 treated with the bacteriocin is observed by scanning electron microscopy (SEM) and transmission electron microscopy (TEM), the cell structure is severely damaged, the cell surface shrinks, membrane holes are formed, and the cytoplasm flows out.

Compared with the prior art, the present disclosure has the following advantages.

1. The present disclosure obtains anti-S. aureus D48 L. rhamnosus ZFM216 bacteriocin from L. rhamnosus ZFM216 fermentation supernatant by macroporous resin adsorption, gel chromatography and reversed-phase HPLC.

2. The present disclosure clarifies that the bacteriostatic mode of L. rhamnosus ZFM216 bacteriocin on S. aureus D48 is cell membrane rupture from intracellular ATP level changes, extracellular conductivity, cell membrane potential difference, and cell microstructure observation.

In summary, the present disclosure obtains the new L. rhamnosus ZFM216 bacteriocin having the potential to be applied to food preservation by establishing an isolation and purification method, and determines the bacteriostatic action mode on methicillin-resistant S. aureus D48.

BRIEF DESCRIPTION OF THE DRAWINGS

Specific implementations of the embodiments of the present disclosure are described in further detail in the following with reference to the accompanying drawings.

FIGS. 1A-1F shows purification and identification of bacteriocin, wherein.

FIGS. 5A-5D are SEM images and TEM images of S. aureus D48 before and after treatment with the L. rhamnosus ZFM216 bacteriocin, wherein:

DETAILED DESCRIPTION

The present disclosure is further described below with reference to specific embodiments, and the advantages and characteristics of the present disclosure become more apparent with the description. However, these examples are only exemplary and do not constitute any limit to the scope of the present disclosure.

The preservation information of L rhamnosus of the present disclosure is as follows: L. rhamnosus ZFM216, preserved at China Center for Type Culture Collection, in Wuhan University, Wuhan, China, with a preservation number of CCTCC NO: M 2020325, on Jul. 17, 2020.

Example 1: Isolation and Purification of L. rhamnosus ZFM216 Bacteriocin (1) Preparation of L. rhamnosus ZFM216 Fermentation Supernatant:

L. rhamnosus ZFM216 stored at −80° C. was streaked on an MRS solid medium plate and cultured at 37° C. After single colonies appeared, the single colonies were picked and cultured in 10 mL of MRS liquid medium to the logarithmic growth phase. 20 mL of MRS liquid medium was inoculated with the cultured solution at an inoculum concentration of 2% (v/v), and subcultured to the logarithmic phase to obtain an inoculum. MRS liquid medium (pH 6.4) was inoculated with the inoculum at an inoculum concentration of 2% (v/v) under optimal culture conditions for performing stationary culture at 37° C. for 21 h. The obtained fermentation broth was centrifuged at 8000 rpm, 4° C. for 30 min to obtain the fermentation supernatant.

(2) Isolation with Macroporous Adsorption Resin Method

Figure 1A:
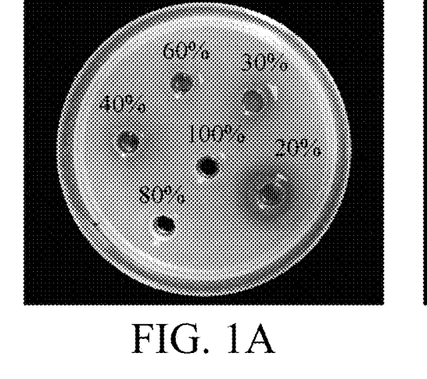
FIG. 1A shows the bacteriostatic activity of a macroporous resin eluate.

1 L of L. rhamnosus ZFM216 fermentation supernatant was allowed to flow through XAD-16 macroporous resin at a flow rate of 2 mL/min, and the unadsorbed supernatant was rinsed off with about 2 L of ultrapure water. Then, 500 mL of 20%, 30%, 40%, 60%, 80%, and 100% ethanol eluents were allowed to flow through the macroporous resin at a flow rate of 2 mL/min, and the eluate obtained under each gradient was collected. The result of a bacteriostatic test with *S. aureus* D48 as the indicator bacteria is shown in FIG. 1A. From FIG. 1A, the 20% ethanol eluate has a good bacteriostatic effect, so the 20% ethanol eluate was used in the subsequent experiments.

(3) Isolation by Gel Chromatography Method

Figure 1B:
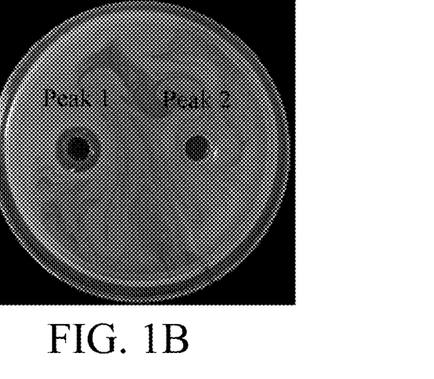
FIG. 1B shows the UV absorption peak of a gel filtration chromatography eluate.
Figure 1C:
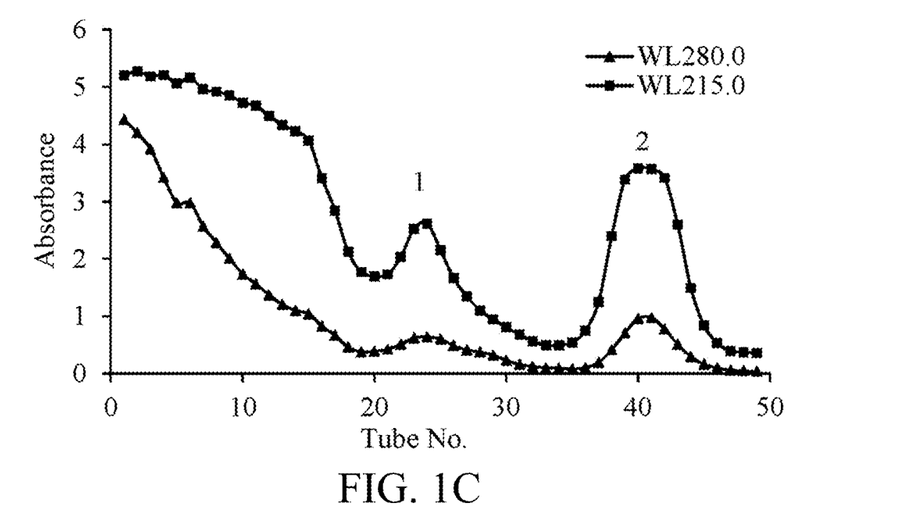
FIG. 1C shows the bacteriostatic activity of a gel eluting peak.

The 20% ethanol eluate obtained in step (2) was used as a crude protein extract with bacteriostatic activity. 20 mL of crude protein extract was subjected to gel chromatography with Sephadex LH-20, and eluted with ultrapure water as the eluent at a flow rate of 1 mL/min. Shown by detection, the absorbance of the eluent at 280 nm/215 nm showed two separate absorption peaks (FIG. 1C). The eluates corresponding to two components were collected (that is, the 21st to 26th tubes were collected as the eluate corresponding to peak 1; the 36th to 45th tubes were collected as the eluate corresponding to peak 2, each tube containing 3 ml of eluate). After concentration, an Oxford cup bacteriostatic test was performed (with *S. aureus* D48 as the indicator bacteria), and the result showed that the peak 1 component had good bacteriostatic activity (FIG. 1B), and the component 1 was collected for subsequent experiments.

(4) Reversed-Phase High Performance Liquid Chromatography (HPLC)

Figure 1D:
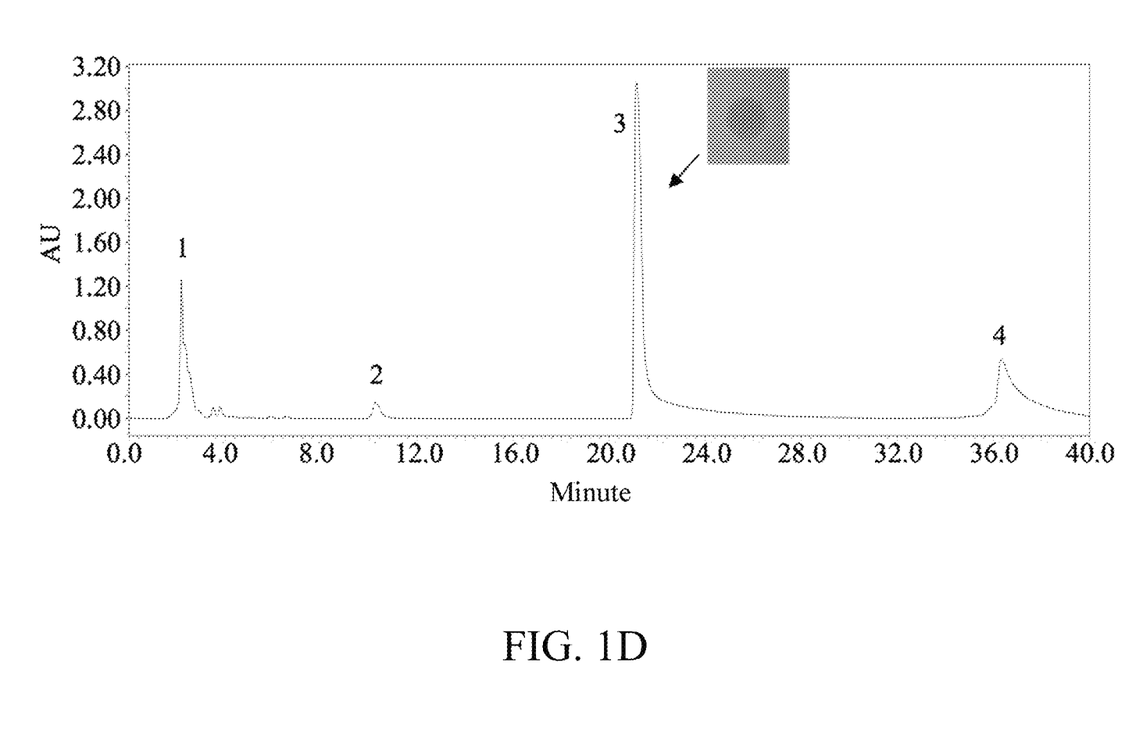
FIG. 1D shows a preparative HPLC purification chromatogram.

The eluate corresponding to the peak 1 obtained in step (3) was collected (that is, the 21st to 26th tubes of eluates were collected), and a total of about 18 mL of eluate (i.e., the collected gel chromatography activity peak 1) was obtained as a preliminary purified protein solution. The preliminary purified protein solution was filtered through a 0.22 μm membrane for later use at 4° C. Precision purification was performed by preparative C18 reversed-phase HPLC (waters 2998, USA), with a chromatographic column Sunfire™ Prep C18 (5 μm×100 mm). The elution procedure is shown in Table 3. The injection volume of the eluate after filtration was 5 mL, a mobile phase A was ultrapure water (containing 0.05% TFA, v/v), and a mobile phase B was acetonitrile (containing 0.05% TFA, v/v). The purification result is shown in FIG. 1D. It can be seen that after purification by HPLC, 4 single peaks were obtained at the absorbance of 280 nm. Each single peak was collected and determined by a spotting samples method (with *S. aureus* D48 as the indicator bacteria) for the bacteriostatic activity, and it was found that peak 3 had better bacteriostatic activity.

That is, specifically, the eluate corresponding to the 3$^{rd}$ absorption peak at the absorbance at 280 nm was collected and named as peak 3 eluate, the peak 3 elutent contains *L. rhamnosus* ZFM216 bacteriocin.

TABLE 3

| \multicolumn{4}{c|}{Elution gradients of mobile phases} |
| Time (min) | Flow rate (mL/min) | Mobile phase A | Mobile phase B |
| --- | --- | --- | --- |
| 0 | 4 | 95 | 5 |
| 15 | 4 | 95 | 5 |
| 16 | 4 | 50 | 50 |
| 26 | 4 | 5 | 95 |
| 30 | 4 | 5 | 95 |
| 31 | 4 | 95 | 5 |
| 45 | 4 | 95 | 5 |

Figure 1E:
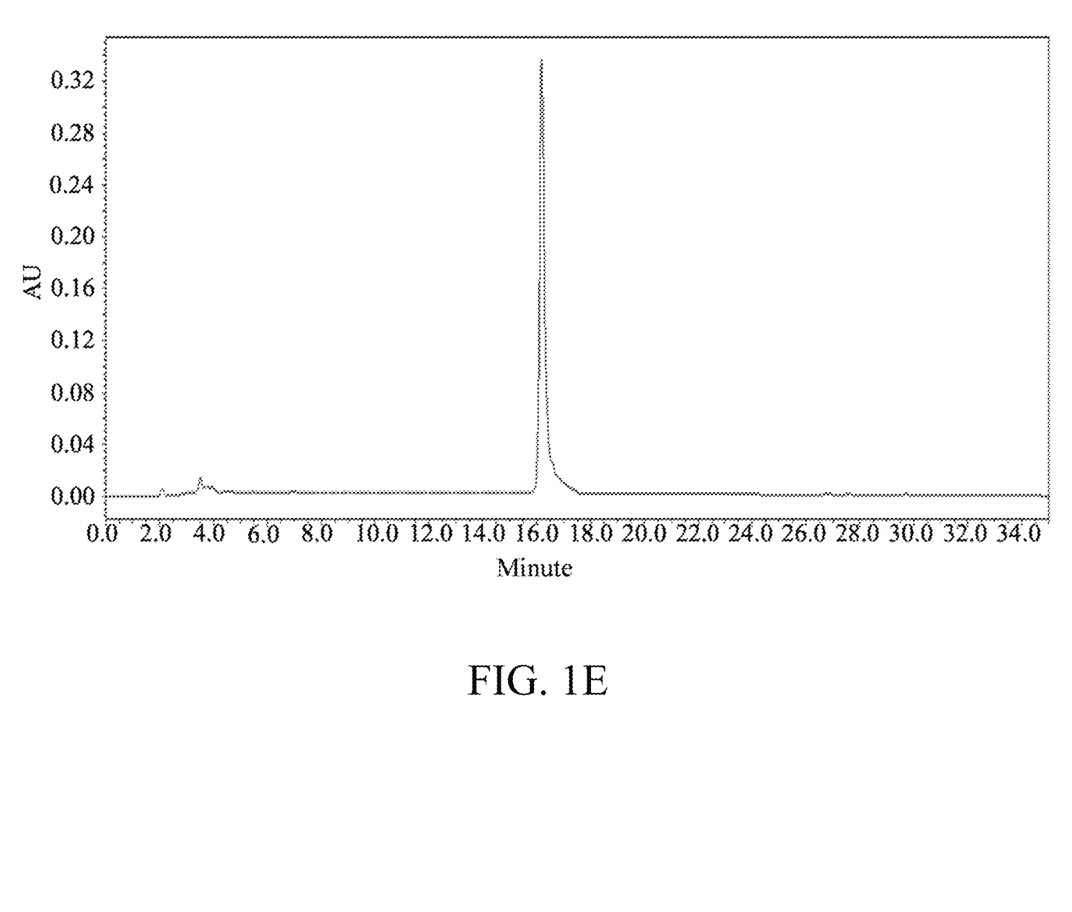
FIG. 1E shows an analytical high performance liquid chromatogram.

(5) Identification of Purity of Bacteriocin by Analytical HPLC 5 mL of the peak 3 eluate (that is, the peak 3 collection with good bacteriostatic activity obtained by preparative HPLC purification in the above step 4) was freeze-dried (at −20° C. to a constant weight) to obtain *L. rhamnosus* ZFM216 bacteriocin, which was reconstituted with 1 mL of ultrapure water to obtain a peak 3 reconstituted solution, that is, an *L. rhamnosus* ZFM216 bacteriocin solution. The purity was detected by analytical HPLC (high performance liquid chromatograph waters 2998, USA) with a chromatographic column Sunfire™ Prep C18 (5 μm, 4.6×250 mm). The elution procedure is shown in Table 4. The mobile phases were the same as step (4) in Example 1, and the injection volume of the peak 3 reconstituted solution was 30 μL. From the chromatogram in FIG. 1E, under the absorbance of 280 nm, a single chromatographic peak appeared at 16.34 min, indicating that bacteriocin was well purified.

TABLE 4

| \multicolumn{4}{c|}{Elution gradients of mobile phases} |
| Time (min) | Flow rate (mL/min) | Mobile phase A | Mobile phase B |
| --- | --- | --- | --- |
| 0 | 0.8 | 95 | 5 |
| 10 | 0.8 | 95 | 5 |
| 11 | 0.8 | 50 | 50 |
| 21 | 0.8 | 5 | 95 |
| 35 | 0.8 | 95 | 5 |

(6) Preestimation of Molecular Weight of Bacteriocin by Tricine-SDS-PAGE

Figure 1F:
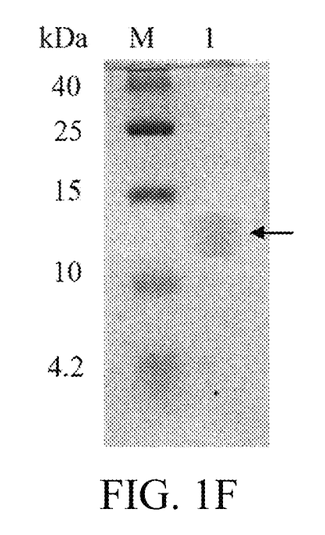
FIG. 1F shows an SDS-PAGE map of L. rhamnosus ZFM216 bacteriocin, where M represents protein Marker, and 1 represents purified L. rhamnosus ZFM216 bacteriocin.

The *L. rhamnosus* ZFM216 bacteriocin solution obtained in step (5) was subjected to SDS-PAGE electrophoresis to estimate the molecular weight of the bacteriocin. As shown in FIG. 1F, the molecular weight of the *L. rhamnosus* ZFM216 bacteriocin is about 13 kDa.

(7) Measurement of Protein Content with BCA Kit Method

The protein content was measured by a BCA kit method. First, a BCA Reagent A and a BCA Reagent B were mixed in a ratio of 100:1 to prepare a working solution. Protein standard product with a concentration gradient of 2000, 1500, 1000, 750, 500, 250, 150 and 0 μg/mL were prepared from a BCA protein standard solution and deionized water. 25 μL of the diluted protein standard solution was added to a 96-well plate, two parallel groups were set for each concentration, and 200 μl of the working solution was added and mixed uniformly and immediately. The mixed solution was treated in a 37° C. water bath for 30 min and cooled to room temperature, and the absorbance was measured at 562 nm using a microplate reader. According to a standard curve with the protein concentration as the X-coordinate and the absorbance as the Y-coordinate, a linear equation y=0.0017x+0.4019 was obtained, and the linear correlation coefficient $R^2$=0.9936.

2.5 μL of the *L. rhamnosus* ZFM216 bacteriocin solution prepared in step (5) was diluted 10 times, and 200 μL of the working solution was added and mixed uniformly and immediately. The mixed solution was treated in a 37° C. water bath for 30 min and cooled to room temperature, and the absorbance was measured at 562 nm using the microplate reader. The *L. rhamnosus* ZFM216 bacteriocin solution was 11.3 mg/mL in protein concentration by equation calculation.

(8) Measurement of Bacteriocin Activity 0.04 g of nisin (with a titer of 1000 IU/mg) was weighed and dissolved in 0.02 M dilute hydrochloric acid to obtain a working solution with a titer of 4000 IU/mL. The working solution was diluted with 0.02 M dilute hydrochloric acid to obtain nisin standard solutions with a concentration gradient of 4000, 2000, 1000, 500, 250, 100, 50 and 0 IU/mL. A bacteriostatic test was performed with *S. aureus* by Oxford cup agar diffusion method, and 100 μL of nisin standard solution was added to the wells of an Oxford cup. The inhibition zone diameter was measured, and a standard curve was drawn with the inhibition zone diameter as the Y-coordinate and the logarithm of the titer of the nisin solution as the X-coordinate. A linear regression equation y=4.005x+6.5668 was obtained, and a linear correlation coefficient $R^2$=0.9974.

100 μL of *L. rhamnosus* ZFM216 bacteriocin solution was added to the wells of an Oxford cup, and the inhibition zone diameter was measured. Based on the equation, the *L. rhamnosus* ZFM216 bacteriocin solution has a total activity of 8805.38 IU, and a specific activity of 778.23 IU/mg.

Example 2: Measurement of Minimum Inhibitory Concentration (MIC) of *L. rhamnosus* ZFM216 Bacteriocin Against *S. aureus* D48

10 mL of LB medium was inoculated with a single colony of *S. aureus* D48, and when $OD_{600}$=0.6, LB liquid medium was inoculated with the culture at an inoculum concentration of 1%. The freeze-dried *L. rhamnosus* ZFM216 bacteriocin obtained in Example 1 was reconstituted and diluted with ultrapure water, and added to a corresponding 96-well plate in a volume of 50 μL to form a final concentration gradient of 2.00 mg/mL, 1.5 mg/mL, 1.00 mg/mL, 7.5 mg/mL, 0.50 mg/mL, 0.25 mg/mL, 0.125 mg/mL, 0.0625 mg/mL, 0.031 mg/mL, and 0 mg/mL. 200 μL of an indicator bacterial solution was added to a 96-well plate in turn. After 12 h, the absorbance was measured at a wavelength of 600 nm, and a bacterial solution without the bacteriocin was used as a control. The result shows that the minimum inhibitory concentration of the *L. rhamnosus* ZFM216 bacteriocin against *S. aureus* D48 is 0.50 mg/mL.

Example 3: Measurement of Effect of *L. rhamnosus* ZFM216 Bacteriocin on ATP Level in *S. aureus* D48

Figure 2:
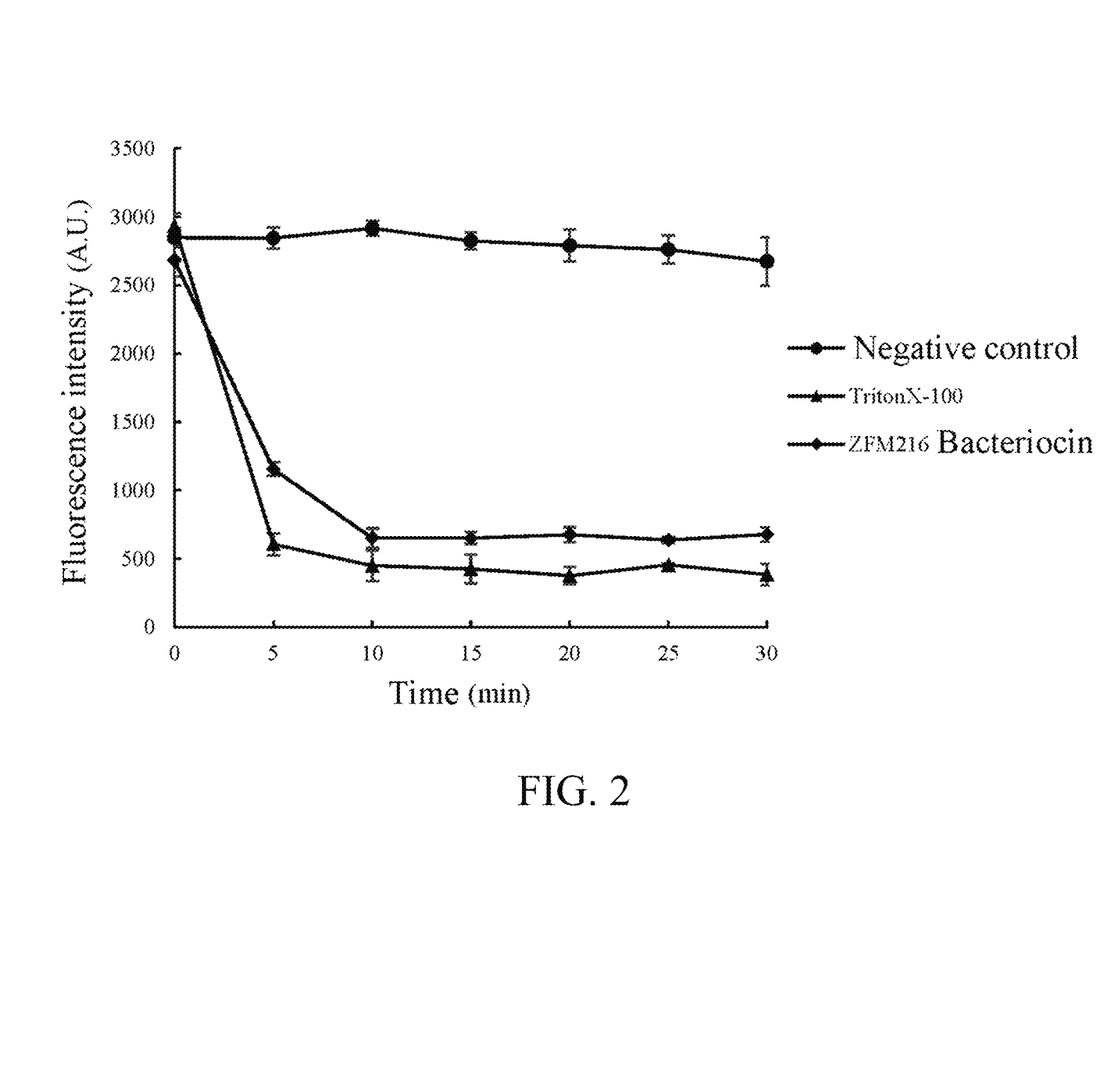
FIG. 2 shows the effect of L. rhamnosus ZFM216 bacteriocin on the ATP level of indicator bacteria.

*S. aureus* D48 was cultured in 10 mL of LB liquid medium at 37° C. to $OD_{600}$=0.6, and centrifuged at 5000 rpm for 20 min to obtain bacterial cells. The bacterial cells were washed with a 5 mM HEPES buffer and reconstituted to 10 mL to obtain a bacterial suspension. 50 μL of a 10 mM glucose solution, 100 μL of the bacterial suspension and 50 μL of the bacteriocin solution were mixed, so that the final concentration of the bacteriocin in the mixture was 0.50 mg/mL. The same volume of a 1% Triton X-100 solution (a surfactant) as the bacteriocin was added in a positive control. The same volume of ultrapure water was added in a negative control. 8 samples were set in each group. A tube was taken every 5 min and centrifuged at 12000 rpm/min for 2 min, and the supernatant was discarded. 25 μL of an ATP detection lysate and 100 μL of an ATP detection reagent working solution were added and resuspended. The fluorescence intensity of the bacterial solution was detected with a multi-function microplate reader. As shown in FIG. 2, the ATP level in the *S. aureus* D48 treated with the *L. rhamnosus* ZFM216 bacteriocin decreased rapidly within 5 min, which was consistent with the trend in the positive control group, while the ATP level in the negative control group remained basically unchanged. The result indicates that the *L. rhamnosus* ZFM216 bacteriocin damaged the cell surface of the *S. aureus* D48 and the cells lost the proton motive force, resulting in an inability of the cells to synthesize ATP and a disorder of intracellular energy metabolism.

Note: The ATP detection lysate and ATP detection reagent working solution are from an ATP detection kit, Cat. No. S0026, purchased from Shanghai Beyotime Biotechnology Co., Ltd.

Example 4: Determination of Effect of *L. rhamnosus* ZFM216 Bacteriocin on Conductivity Level of *S. aureus* D48

Figure 3:
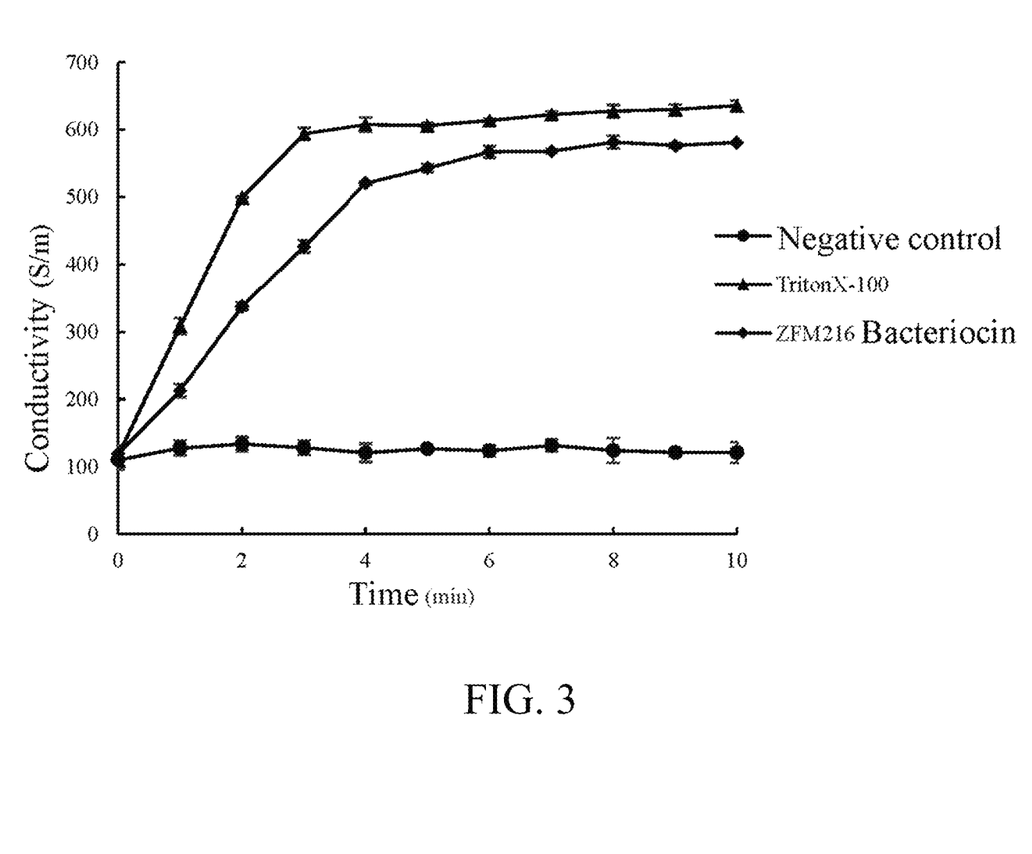
FIG. 3 shows the effect of L. rhamnosus ZFM216 bacteriocin on the conductivity of indicator bacteria.

An *S. aureus* D48 bacterial suspension was prepared by the preparation method same as that in Example 3. An electrode probe of a conductivity meter was inserted into the bacterial suspension and the initial conductivity was recorded. In the experimental group, a bacteriocin solution with a final concentration of 1×MIC was quickly added. An equal volume of a 1% Triton X-100 solution was added in a positive control group, and an equal volume of an HEPES buffer was added in a negative control group. Readings were taken every 1 min until the value stabilized. As shown in FIG. 3, after the *L. rhamnosus* ZFM216 bacteriocin was added, the conductivity of the *S. aureus* D48 bacterial suspension increased to the highest value within 5 min and remained stable, which was consistent with the trend in the positive control group, while the conductivity in the negative control group remained basically unchanged. The result indicates that the *L. rhamnosus* ZFM216 bacteriocin damaged the cell membrane of the *S. aureus* D48 and caused efflux of intracellular electrolytes.

Example 5: Measurement of Effect of *L. rhamnosus* ZFM216 Bacteriocin on Membrane Potential Difference of *S. aureus* D48

Figure 4:
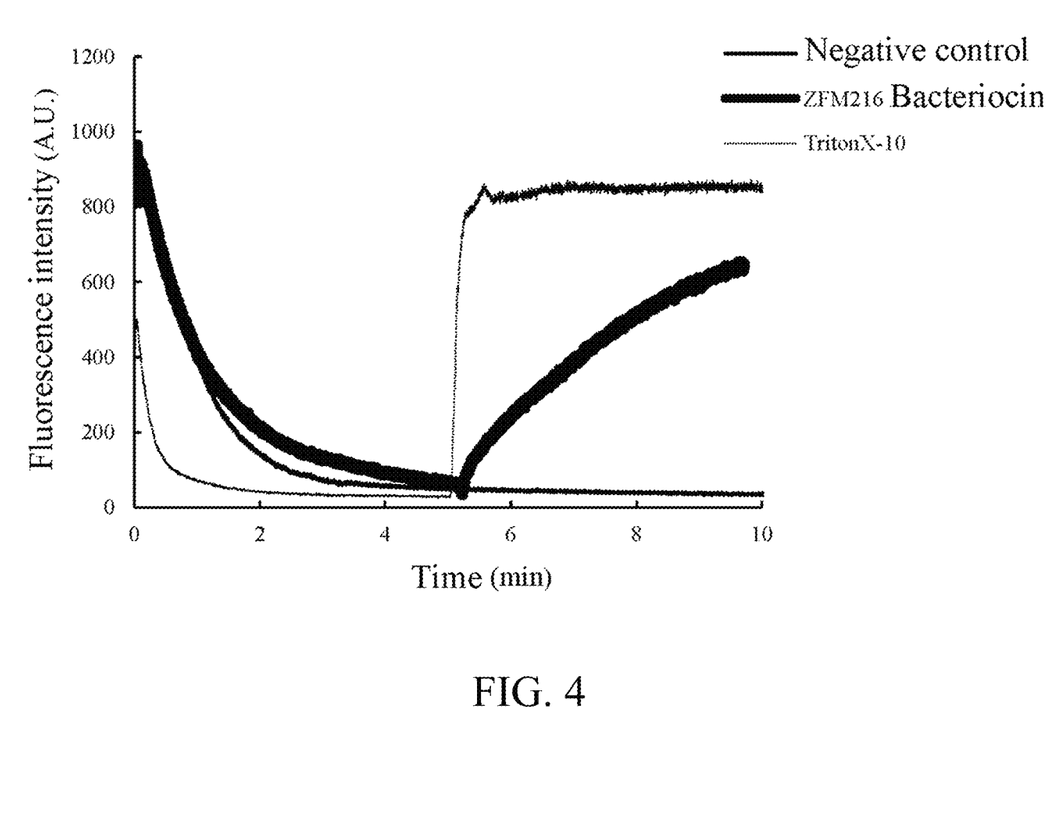
FIG. 4 shows the effect of L. rhamnosus ZFM216 bacteriocin on the cell membrane potential difference of indicator bacteria.

*S. aureus* D48 cells were prepared by the same method as that in Example 3, washed with a 5 mM fluorescent leakage buffer and resuspended to 5 mL to obtain a bacterial suspension. A fluorescent probe $DiSC_2(5)$ was set to have an excitation wavelength of 650 nm and an emission wavelength of 670 nm. The scanning interval was set as Ex slit: 5 nm, Em slit: 5 nm, and the scanning time was 15 min. 2 mL of the fluorescent leakage buffer, 20 μL of the bacterial suspension, and 3 μL of 0.1 mM probe $DiSC_2(5)$ were added to a fluorescence cuvette, and mixed uniformly for detection. After the fluorescence response value became stable, the *L. rhamnosus* ZFM216 bacteriocin solution with a final concentration of 1×MIC was quickly added in the experimental group, and the same volume of fluorescence leakage buffer and 5% Triton X-100 solution were added to the control groups respectively. As shown in FIG. 4, the fluorescence intensity in the *S. aureus* D48 bacterial suspension added with the *L. rhamnosus* ZFM216 bacteriocin increased with time, the fluorescence intensity of the *S. aureus* D48 treated with the TritonX-100 in the positive control group rapidly increased to the highest value, while the fluorescence intensity in the negative control group remained unchanged. The result indicates that the *L. rhamnosus* ZFM216 bacteriocin damaged the cell membrane of the *S. aureus* D48, resulting in leakage of intracellular fluorescent probes.

Note: The preparation method of the fluorescent leakage buffer is: 0.7455 g of potassium chloride and 0.2463 g of a magnesium sulfate heptahydrate solution are accurately weighed, 22.5 mL of a 20% glucose solution and 10 mL of a phosphate buffer solution are measured, the volume is diluted to 100 mL with ultrapure water, the pH is adjusted to 7, and the prepared fluorescent leakage buffer is stored at 4° C. for later use.

Example 6: Observation of Effect of L. rhamnosus ZFM216 Bacteriocin on Microstructure of S. aureus D48 Cells (SEM and TEM)

(1) SEM Observation

Figure 5A:
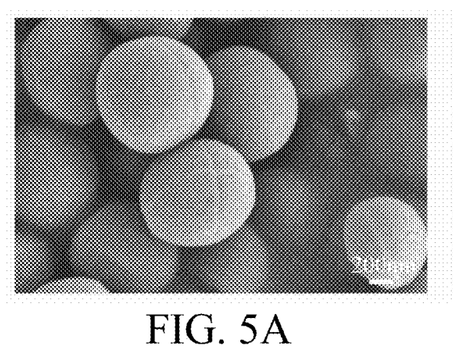
FIG. 5A is the SEM image of untreated S. aureus D48.
Figure 5B:
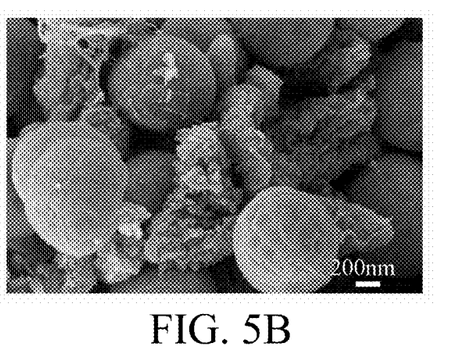
FIG. 5B is the SEM image of S. aureus D48 treated with L. rhamnosus ZFM216 bacteriocin for 1 h.

S. aureus D48 was cultured to $OD_{600}$=0.6, an L. rhamnosus ZFM216 bacteriocin solution with a final concentration of 3×MIC was added, and an equal volume of phosphate buffer (pH 7.0) was added in the control group, and incubated at 37° C. for 1 h. The bacterial solution was centrifuged at 6000 rpm for 15 min, and the supernatant was discarded. After being rinsed with a 0.1 M phosphate buffer (pH 7.0), the cells were fixed with a 2.5% glutaraldehyde solution at 4° C. for 12 h. The cells were rinsed with a 0.1 M phosphate buffer, and centrifuged at 6000 rpm/min for 15 min, and the supernatant was discarded. The samples were then fixed with a 1% osmic acid solution for 2 h to obtain double-fixed cells. The double-fixed cells were dehydrated with 30%-100% ethanol solutions (10% increments) in turn for 15 min each, and the supernatant was discarded. The cells were treated with 100% ethanol for 20 min, and centrifuged to discard the supernatant. The cells were dried at the critical point and coated, and the samples were observed. As shown in FIG. 5A, the untreated S. aureus D48 had complete cell structure and smooth and rounded cell membrane surface. As shown in FIG. 5B, the S. aureus D48 treated with the L. rhamnosus ZFM216 bacteriocin showed cell surface shrinkage, cell rupture and complete lysis of some cells.

(2) TEM Observation

Figure 5C:
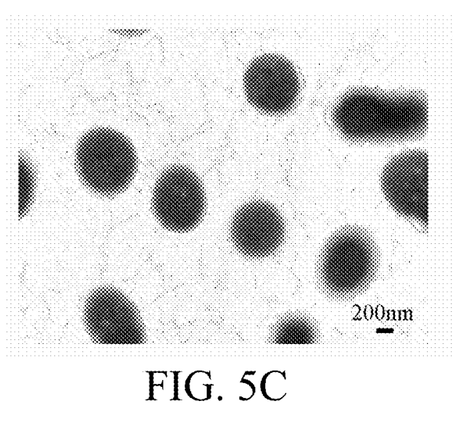
FIG. 5C is the TEM image of untreated S. aureus D48.
Figure 5D:
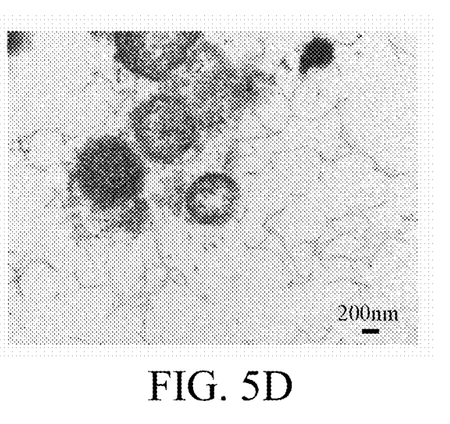
FIG. 5D is THE TEM image of S. aureus D48 treated with L. rhamnosus ZFM216 bacteriocin for 1 h.

Double-fixed cells were prepared by the same method as that in Example 6(1), and dehydrated with 30%-95% ethanol solutions (10% increments) in turn for 15 min each, and the supernatant was discarded. Then the cells were treated with 100% ethanol for 20 min, and finally treated with pure acetone for 20 min, and the supernatant was discarded. The samples were treated with mixtures of an embedding agent and acetone in volume ratios of 1:1 and 3:1 respectively for 1 h and 3 h, and the samples were treated with the pure embedding agent overnight. The embedded samples were heated at 70° C. for 12 h and cooled. Sections with a thickness of 70-90 nm were obtained, and stained with a lead citrate solution and a uranyl acetate solution for 5-10 min respectively, and the samples were observed. As shown in FIG. 5C, the untreated S. aureus D48 cells had a complete cell structure, a typical and complete cell wall and membrane structure, and evenly distributed and dense cytoplasm. However, as shown in FIG. 5D, the structure of cells treated with the L. rhamnosus ZFM216 bacteriocin was severely damaged, the cell membrane and cell wall were damaged to a certain extent, and the cytoplasm flew out.

Comparative Example 1: During isolation with macroporous adsorption resin method, instead of the eluate corresponding to 20% ethanol, the eluates corresponding to 30%, 40%, 60%, 80% and 100% ethanol were collected. The result shows that the collected eluates generally had no bacteriostatic effects on S. aureus.

Comparative Example 2: During isolation by gel chromatography method, instead of the eluate corresponding to component 1, the eluate corresponding to component 2 was collected for subsequent operations. The result shows that the collected eluate generally had no bacteriostatic effects on S. aureus.

Comparative Example 3: During isolation by high performance liquid chromatography method, instead of the eluate corresponding to peak 3, the eluates corresponding to peak 1, peak 2 and peak 4 were collected. The result shows that the collected eluates generally had no bacteriostatic effects on S. aureus.

Finally, it should also be noted that the above enumeration is only a few specific embodiments of the present disclosure. Obviously, the present disclosure is not limited to the foregoing embodiments, and there may further be many modifications. All deformations that a person of an ordinary skill in the art can directly derive or associate from the content disclosed in the present disclosure shall be considered as the protection scope of the present disclosure.

What is claimed is:

1. A method for isolating and purifying Lactobacillus rhamnosus ZFM216 bacteriocin, comprising the following steps:
   1) preparing L. rhamnosus ZFM216 fermentation supernatant:
      inoculating MRS liquid medium with L. rhamnosus ZFM216 for fermentation, and
      centrifuging the fermentation broth to obtain the fermentation supernatant;
      the preservation number of L. rhamnosus ZFM216 being CCTCC M 2020325;
   2) treating the fermentation supernatant with macroporous adsorption resin to obtain a crude protein extract;
   3) isolating the crude protein extract by gel chromatography to obtain a preliminary purified protein solution; and then performing purification by reversed-phase high performance liquid chromatography (RP-HPLC) to obtain an L. rhamnosus ZFM216 bacteriocin solution;
   wherein in step 1), MRS liquid medium, pH 6.4, is inoculated with L. rhamnosus ZFM216 cultured to the logarithmic growth phase at an inoculum concentration of 2% v/v for performing stationary culture at 37° C. for 21 h; and the obtained fermentation broth is centrifuged at 8000 rpm, 4° C., for 30 min to obtain the fermentation supernatant;
   in step 2), 1 L of the fermentation supernatant is allowed to flow through the macroporous adsorption resin, rinsed with 2 L of ultrapure water at a flow rate of 2 mL/min, and then eluted with 500 mL of 20% ethanol at a flow rate of 2 mL/min, and the eluate is a crude protein extract; and
   during the isolation by gel chromatography in step 3), the crude protein extract is subjected to gel chromatography and eluted with ultrapure water as the eluent at a flow rate of 1 mL/min; and the eluate corresponding to the first absorption peak under the absorbance of 215 nm/280 nm is collected to obtain a preliminary purified protein solution; and then the preliminary purified protein solution is filtered through a 0.22 m membrane, and precisely purified by preparative C18 reversed-phase high performance liquid chromatography (RP-HPLC) with a chromatographic column at an injection volume of 5 mL to obtain an L. rhamnosus ZFM216 bacteriocin solution.

2. The method according to claim 1, wherein 0.05% trifluoroacetic acid (TFA) by volume of ultrapure water is added to the ultrapure water as mobile phase A, and 0.05% TFA by volume of acetonitrile is added to the acetonitrile as mobile phase B; the gradient elution procedure is as follows:

| Time (min) | Flow rate (mL/min) | Mobile phase A | Mobile phase B |
|---|---|---|---|
| 0 | 4 | 95 | 5 |
| 15 | 4 | 95 | 5 |
| 16 | 4 | 50 | 50 |
| 26 | 4 | 5 | 95 |
| 30 | 4 | 5 | 95 |
| 31 | 4 | 95 | 5 |
| 45 | 4 | 95 | 5 | the eluate corresponding to the $3^{rd}$ absorption peak under the absorbance of 280 nm is collected, and named as peak 3 eluate, the peak 3 eluate contains *L. rhamnosus* ZFM216 bacteriocin.

3. The method according to claim 2, wherein 5 mL of peak 3 eluate is freeze-dried to obtain *L. rhamnosus* ZFM216 bacteriocin, which is reconstituted with 1 ml of ultrapure water to obtain a peak 3 reconstituted solution, that is, the peak 3 reconstituted solution is an *L. rhamnosus* ZFM216 bacteriocin solution.

\* \* \* \* \*